US00PP30118P2

(12) United States Plant Patent
Kievit

(10) Patent No.: US PP30,118 P2
(45) Date of Patent: Jan. 15, 2019

(54) ***SALVIA* PLANT NAMED 'ROSE MARVEL'**

(50) Latin Name: *Salvia nemorosa*
Varietal Denomination: Rose Marvel

(71) Applicant: Ball Horticultural Company, West Chicago, IL (US)

(72) Inventor: Christa Kievit, Hem (NL)

(73) Assignee: Ball Horticultural Company, West Chicago, IL (US)

( * ) Notice: Subject to any disclaimer, the term of this patent is extended or adjusted under 35 U.S.C. 154(b) by 5 days.

(21) Appl. No.: 15/731,901

(22) Filed: Aug. 21, 2017

(51) Int. Cl.
*A01H 5/02* (2018.01)

(52) U.S. Cl.
USPC ..... Plt./475
CPC ..... *A01H 5/02* (2013.01)

(58) Field of Classification Search
USPC ..... Plt./475
See application file for complete search history.

*Primary Examiner* — Anne Marie Grunberg
(74) *Attorney, Agent, or Firm* — Audrey Charles

(57) ABSTRACT

A new and distinct cultivar of *Salvia* plant named 'Rose Marvel', characterized by its deep purple-violet with red-purple colored flowers, medium green-colored foliage, and moderately vigorous, upright-mounded growth habit, is disclosed.

1 Drawing Sheet

Latin name of genus and species of plant claimed: *Salvia nemorosa.*

Variety denomination: 'Rose Marvel'.

BACKGROUND OF THE INVENTION

The present invention relates to a new and distinct cultivar of *Salvia* plant botanically known as *Salvia nemorosa* and hereinafter referred to by the cultivar name 'Rose Marvel'.

The new cultivar originated in a controlled breeding program in Venhuizen, The Netherlands during August 2013. The objective of the breeding program was the development of a *Salvia* cultivar having large flowers and compact growth habits.

The new *Salvia* cultivar was the result of a self-pollination of the proprietary *Salvia nemorosa* breeding selection coded M118-1, not patented, characterized by its medium violet-blue colored flowers, medium green-colored foliage, and moderately vigorous, semi-upright growth habit. The new cultivar was discovered and selected as a single flowering plant within the progeny of the above stated self-pollination during July 2014 in a controlled environment in Venhuizen, The Netherlands.

Asexual reproduction of the new cultivar by terminal stem cuttings since July 2014 in Venhuizen, The Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Rose Marvel' as a new and distinct cultivar of *Salvia* plant:

1. Deep purple-violet with red-purple colored flowers;
2. Medium green-colored foliage; and
3. Moderately vigorous, upright-mounded growth habit.

Plants of the new cultivar differ from plants of the parent primarily in having a different flower color, and a more upright growth habit.

Of the many commercially available *Salvia* cultivars, the most similar in comparison to the new cultivar is 'Blue Marvel', U.S. Plant Pat. No. 27,018. However, in side by side comparisons, plants of the new cultivar differ from plants of 'Blue Marvel' in at least the following characteristics:

1. Plants of the new cultivar have a flower color different from plants of 'Blue Marvel';
2. Plants of the new cultivar have larger corollas than plants of 'Blue Marvel'; and
3. Plants of the new cultivar have larger sized leaves than plants of 'Blue Marvel'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Rose Marvel'. The plants were 15 weeks old and grown in one-gallon containers for approximately 4 weeks in a greenhouse and 5 weeks outdoors in Elburn, Ill. Plants were given one pinch two weeks after transplant.

DETAILED BOTANICAL DESCRIPTION

Figure 1:
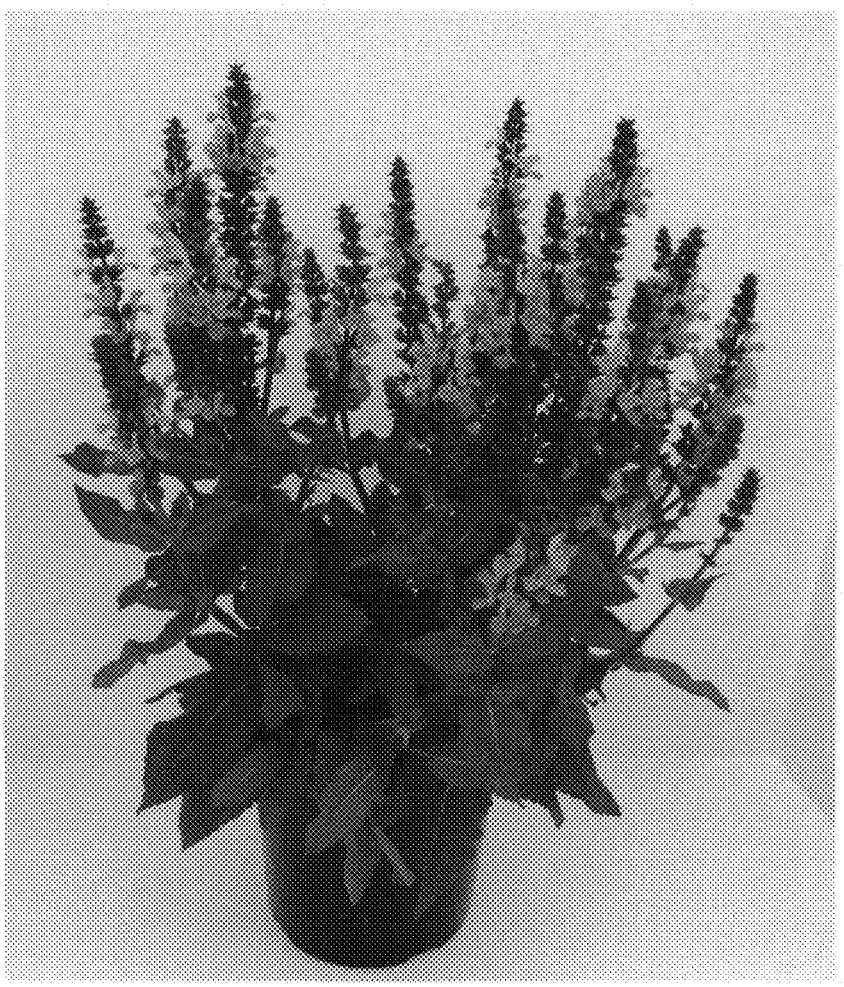
FIG. 1 illustrates a side view of the overall growth and flowering habit of 'Rose Marvel'.
Figure 2:
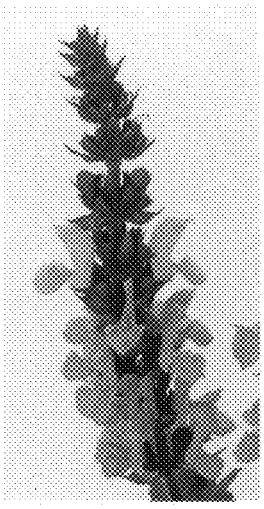
FIG. 2 illustrates a close-up view of an individual inflorescence of 'Rose Marvel'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in June 2017 under natural light conditions in West Chicago, Ill.

The following descriptions and measurements describe 15 week old plants produced from cuttings from stock plants and grown under conditions comparable to those used in commercial practice. The plants were grown in 1 gallon containers for approximately 4 weeks in a greenhouse and 5 weeks outdoors in Elburn, Ill. Plants were given one pinch two weeks after transplant. Greenhouse temperatures were maintained at approximately 72° F. (22.2° C.) during the day and approximately 62° F. (16.7° C.) during the night. No supplemental lighting was provided. Measurements and numerical values represent averages of typical plants.

Botanical classification: *Salvia nemorosa* 'Rose Marvel'.

Parentage:

*Female and male parent*.—Proprietary *Salvia nemorosa* breeding selection coded M118-1, not patented.

Propagation:

*Type cutting*.—Terminal stem.

*Time to initiate roots*.—Approximately 12 to 15 days.

*Time to produce a rooted cutting*.—Approximately 35 to 42 days.

*Root description*.—Fine, fibrous, typically white to dark brown in color.

*Rooting habit*.—Freely branching.

Plant description:

*Commercial crop time*.—Approximately 12 to 14 weeks from a rooted cutting to finish in a 15 cm pot.

*Growth habit and general appearance*.—Moderately vigorous, upright growth habit.

*Plant type*.—Herbaceous perennial.

*Hardiness*.—USDA zones 4a to 9b.

*Size*.—Height from soil level to top of plant plane: Approximately 40.0 cm. Width: Approximately 33.0 cm.

*Branching habit*.—Freely branching. Pinching enhances lateral branching. Quantity of branches per plant: Approximately 3 main branches with approximately 18 lateral branches.

*Branch*.—Shape: Square in cross section. Strength: Strong. Length to base of inflorescence: Approximately 17.0 cm. Diameter: Approximately 7.0 mm. Length of central internode: Approximately 5.0 cm. Texture: Densely pubescent. Color of young stems: 146B with streaks of 187A. Color of mature stems: 146A with streaks to a complete overlay of 187A, becoming woody 200C with age.

Foliage description:

*General description*.—Quantity of leaves per main branch: Approximately 6. Fragrance: Strong, sage-like. Form: Simple. Arrangement: Opposite.

*Leaves*.—Aspect: Acute to perpendicular angle to stem. Shape: Ovate to elliptic. Margin: Crenate. Apex: Acute. Base: Cordate. Venation pattern: Pinnate. Length of mature leaf: Approximately 9.5 cm. Width of mature leaf: Approximately 5.0 cm. Texture of upper surface: Rugose, sparsely pubescent with very short hairs. Texture of lower surface: Rugose, densely pubescent with very short hairs. Color of upper surface of young foliage: 138A with midvein of 145D. Color of lower surface of young foliage: Closest to N138B with venation of 145C. Color of upper surface of mature foliage: Closest to 137A with venation of 145C. Color of lower surface of mature foliage: Closest to between N138A and N138B with venation of 145C.

*Petiole*.—Length: Approximately 2.0 cm. Diameter: Approximately 4.0 mm. Texture: Densely pubescent. Color: Closest to 146D.

Flowering description:

*Flowering habit*.—'Rose Marvel' is freely flowering under outdoor growing conditions with substantially continuous blooming from early spring through late summer and with limited flowering under short winter days in a greenhouse environment.

*Lastingness of individual floret*.—Approximately 4 to 5 days.

Inflorescence description:

*General description*.—Type: Spikes in verticillaster arrangement, florets in clusters of two to three, not persistent. Quantity of inflorescences per plant: Approximately 24. Fragrance: Faint, sweet. Length or height of inflorescence: Approximately 9.0 cm to 18.5 cm. Width of inflorescence: Approximately 3.0 cm to 3.5 cm. Quantity of fully-open flowers per inflorescence: Approximately 16 with up to 40 at peak flowering.

*Peduncle*.—Shape: Square in cross section. Strength: Strong. Aspect: Erect. Length: Approximately 2.0 cm to 3.5 cm. Diameter: Approximately 2.0 mm to 4.0 mm. Texture: Densely pubescent. Color: 146B with streaks of 187A.

Flower description:

*Type*.—Single, zygomorphic.

*Bud*.—Rate of opening: Generally takes 2 to 3 days for bud to progress from first color to fully open flower.

*Bud just before opening*.—Shape: Obovoid. Length: Approximately 9.0 mm. Diameter: Approximately 5.0 mm. Texture: Densely pubescent. Color: Calyx of 187A with venation of 187B and 146C at base; petal portion of 71B.

*Corolla*.—Shape: Bilabiate, lower lip having three lobes, base fused. Width: Approximately 9.0 mm. Length: Approximately 1.6 cm. Depth: Approximately 1.9 cm.

*Upper lip*.—Shape: Hooded. Margin: Entire. Apex: Rounded. Length from throat: Approximately 1.0 cm. Width: Approximately 1.0 mm. Texture of inner surface: Glabrous. Texture of outer surface: Moderately pubescent. Color of inner surface when first and fully open: 75B. Color of outer surface when first and fully open: 70B to 70C.

*Lower lip*.—Shape of central lobe: Orbicular, cupped. Shape of lateral lobes: Oblong. Margin: Entire, central lobe wavy. Apex of central lobe: Emarginate. Apex of lateral lobes: Rounded. Length from throat of central lobe: Approximately 7.0 mm. Width of central lobe: Approximately 9.0 mm. Length from throat of lateral lobes: Approximately 4.0 mm. Width of lateral lobes: Approximately 3.0 mm. Texture of upper surface: Glabrous. Texture of lower surface: Sparsely pubescent. Color of upper surface when first and fully open: lateral lobes of 70A to 70B, central lobe N81B to N81C. Color of lower surface when first and fully open: lateral lobes of 70B to 70C, central lobe N81C.

*Corolla tube*.—Length: Approximately 5.0 mm. Diameter at opening: Approximately 4.0 mm. Diameter at base: Approximately 2.0 mm. Texture of inner and outer surfaces: Glabrous. Color of inner surface when first and fully open: NN155D. Color of outer surface when first and fully open: NN155D.

*Calyx*.—Shape: Cupped. Length: Approximately 7.0 mm. Diameter: Approximately 6.0 mm.

*Sepals*.—Quantity per flower: 5, fused. Shape: Ovate. Apex: Acute. Length: Approximately 7.0 mm. Width of lobes: Approximately 2.0 mm to 3.0 mm. Texture of inner and outer surfaces: Densely pubescent. Color of inner surface: 137C. Color of outer surface: 187A with 144B at base.

*Bracts*.—Quantity: One bract located at the base of floret cluster. Shape: Ovate. Apex: Acuminate. Texture of inner (upper) surface: Glabrous. Texture of outer (lower) surface: Densely pubescent. Color of inner and outer surfaces: 137B with and overlay of N186C to N186D.

*Pedicel*.—Strength: Strong, flexible. Aspect: At an acute angle. Length: Approximately 2.0 mm. Diameter: Less than 1.0 mm. Texture: Densely pubescent. Color: 145B with a heavy overlay of 187A.

*Reproductive organs*.—Androecium: Stamen quantity: 2 per flower, dorsifixed, strongly curved. Stamen length: Approximately 1.2 cm. Filament length: Approximately 1.0 cm. Filament color: NN155D with a faint overlay of 70B at base. Anther shape: Oblong. Anther length: Approximately 2.0 mm. Anther color: 161B with 185A. Pollen amount: Abundant. Pollen color: 4D. Gynoecium: Pistil quantity: 1 per flower, slightly curved. Pistil length: Approximately 1.7 cm. Stigma shape: Cleft, two-parted. Stigma length: 2.0 mm. Stigma color: N81A. Style length: Approximately 1.3 cm. Style color: NN155D. Ovary length: Approximately 2.0 mm. Ovary color: 144C with 23A.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Rose Marvel', substantially as herein illustrated and described.

* * * * *